US009918657B2

(12) United States Patent
Daon et al.

(10) Patent No.: US 9,918,657 B2
(45) Date of Patent: Mar. 20, 2018

(54) METHOD FOR DETERMINING THE LOCATION AND ORIENTATION OF A FIDUCIAL REFERENCE

(71) Applicant: Navigate Surgical Technologies, Inc., Vancouver (CA)

(72) Inventors: Ehud (Udi) Daon, North Vancouver (CA); Martin Gregory Beckett, Bowen Island (CA); Alvaro Andres Medina Rodriguez, Vancouver (CA)

(73) Assignee: Navigate Surgical Technologies, Inc., Vancouver, BC (CA)

( * ) Notice: Subject to any disclaimer, the term of this patent is extended or adjusted under 35 U.S.C. 154(b) by 330 days.

(21) Appl. No.: 14/458,205

(22) Filed: Aug. 12, 2014

(65) Prior Publication Data
US 2016/0045279 A1 Feb. 18, 2016

Related U.S. Application Data

(63) Continuation-in-part of application No. 14/226,708, filed on Mar. 26, 2014, which is a
(Continued)

(51) Int. Cl.
*A61B 5/05* (2006.01)
*A61B 5/055* (2006.01)
(Continued)

(52) U.S. Cl.
CPC .............. *A61B 5/055* (2013.01); *A61B 6/032* (2013.01); *A61B 8/14* (2013.01); *A61B 19/52* (2013.01);
(Continued)

(58) Field of Classification Search
CPC ....... A61B 5/05; A61B 5/1127; A61B 19/203; A61B 19/56; A61B 19/5244; A61B 19/22;
(Continued)

(56) References Cited

U.S. PATENT DOCUMENTS

| 5,230,623 A | 7/1993 | Guthrie |
| 5,438,991 A | 8/1995 | Yu et al. |

(Continued)

FOREIGN PATENT DOCUMENTS

| DE | 10 2005 026654 | 12/2006 |
| DE | 2009009158 | 9/2010 |

(Continued)

OTHER PUBLICATIONS

European Patent Office, International Search Report, dated Sep. 3, 2013 (PCT/IL2013/000032).

(Continued)

*Primary Examiner* — Joel Lamprecht
(74) *Attorney, Agent, or Firm* — Kevin R. Erdman; Brannon Sowers & Cracraft PC

(57) ABSTRACT

A method for determining the 3D location and orientation of a fiducial reference comprises disposing the fiducial reference so as to render a part of the fiducial reference observable by a tracker; obtaining from the tracker scan data of the part of the fiducial reference that is observable by the tracker; obtaining predetermined geometric information about location points on the fiducial reference, the geometric information containing three-dimensional coordinates of the location points relative to the structure of the fiducial reference; identifying within the scan data at least three location points having coordinates in the predetermined geometric information; and determining from the scan data and the coordinates of the three identified location points in the predetermined geometric information the 3D location and orientation of the fiducial reference.

16 Claims, 13 Drawing Sheets

Related U.S. Application Data continuation-in-part of application No. 13/713,165, filed on Dec. 13, 2012, now Pat. No. 8,908,918, said application No. 14/226,708 is a continuation-in-part of application No. PCT/EP2013/073401, filed on Nov. 8, 2013.

(60) Provisional application No. 61/865,508, filed on Aug. 13, 2013, provisional application No. 61/724,024, filed on Nov. 8, 2012.

(51) Int. Cl.

| | | |
|---|---|---|
| A61C 3/00 | (2006.01) | |
| A61C 19/00 | (2006.01) | |
| A61B 6/03 | (2006.01) | |
| A61B 8/14 | (2006.01) | |
| A61B 19/00 | (2006.01) | |
| A61B 34/20 | (2016.01) | |
| A61B 90/98 | (2016.01) | |
| A61B 90/00 | (2016.01) | |
| A61B 34/10 | (2016.01) | |

(52) U.S. Cl.
CPC .............. *A61B 19/54* (2013.01); *A61B 34/20* (2016.02); *A61B 90/98* (2016.02); *A61C 3/00* (2013.01); *A61C 19/00* (2013.01); *A61B 2019/5287* (2013.01); *A61B 2019/5483* (2013.01); *A61B 2034/101* (2016.02); *A61B 2034/2065* (2016.02); *A61B 2090/363* (2016.02); *A61B 2090/371* (2016.02); *A61B 2090/3966* (2016.02); *A61B 2090/3983* (2016.02)

(58) Field of Classification Search
CPC .............. A61B 19/50; A61B 2019/481; A61B 2019/507; A61B 2019/5255; A61B 2019/5248
See application file for complete search history.

(56) References Cited

U.S. PATENT DOCUMENTS

| | | | |
|---|---|---|---|
| 5,603,318 A | 2/1997 | Heilbrun et al. | |
| 5,828,770 A | 10/1998 | Leis et al. | |
| 5,967,777 A | 10/1999 | Klein | |
| 6,122,541 A | 9/2000 | Cosman et al. | |
| 6,468,265 B1 | 10/2002 | Evans et al. | |
| 6,529,765 B1 | 3/2003 | Franck et al. | |
| 7,176,936 B2 * | 2/2007 | Sauer ...................... G06F 3/011 345/592 | |
| 7,653,455 B2 | 1/2010 | Cinador | |
| 7,720,521 B2 | 5/2010 | Chang | |
| 7,758,345 B1 | 7/2010 | Christensen | |
| 7,894,878 B2 | 2/2011 | Noujeim | |
| 7,899,512 B2 | 3/2011 | Labadie | |
| 8,172,573 B2 | 5/2012 | Sonenfeld | |
| 8,911,499 B2 * | 12/2014 | Quaid .................. A61B 17/1764 623/18.11 | |
| 2004/0002642 A1 | 1/2004 | Dekel et al. | |
| 2004/0097952 A1 | 5/2004 | Sarin et al. | |
| 2004/0138556 A1 | 7/2004 | Cosman | |
| 2005/0085719 A1 | 4/2005 | Franklin et al. | |
| 2005/0163342 A1 | 7/2005 | Persky | |
| 2005/0182318 A1 | 8/2005 | Kaji et al. | |
| 2006/0142657 A1 | 6/2006 | Quaid et al. | |
| 2006/0165310 A1 | 7/2006 | Mack | |
| 2006/0212044 A1 | 9/2006 | Bova et al. | |
| 2006/0247517 A1 | 11/2006 | Labadie et al. | |
| 2006/0281991 A1 | 12/2006 | Fitzpatrick | |
| 2007/0208252 A1 | 9/2007 | Makower | |
| 2007/0223910 A1 | 9/2007 | Aoki | |
| 2007/0253541 A1 | 11/2007 | Sukovic et al. | |
| 2008/0026338 A1 | 1/2008 | Cinader | |
| 2008/0135733 A1 | 6/2008 | Feilkas | |
| 2008/0161682 A1 | 7/2008 | Kendrick et al. | |
| 2008/0171305 A1 | 7/2008 | Sonenfeld et al. | |
| 2008/0183071 A1 | 7/2008 | Strommer | |
| 2008/0193896 A1 | 8/2008 | Yang | |
| 2008/0200927 A1 | 8/2008 | Hartmann et al. | |
| 2008/0262345 A1 | 10/2008 | Fichtinger | |
| 2008/0319491 A1 | 12/2008 | Schoenefeld | |
| 2009/0012509 A1 | 1/2009 | Csavoy | |
| 2009/0171196 A1 | 7/2009 | Olson et al. | |
| 2009/0253095 A1 | 10/2009 | Salcedo | |
| 2010/0039506 A1 | 2/2010 | Sarvestani et al. | |
| 2010/0049195 A1 | 2/2010 | Park et al. | |
| 2010/0168562 A1 | 7/2010 | Zhao et al. | |
| 2010/0168763 A1 | 7/2010 | Zhao et al. | |
| 2010/0210939 A1 | 8/2010 | Hartmann et al. | |
| 2010/0217139 A1 | 8/2010 | Pinter et al. | |
| 2010/0298712 A1 | 11/2010 | Pelissier et al. | |
| 2011/0008751 A1 | 1/2011 | Patterssen | |
| 2011/0087332 A1 | 4/2011 | Bojarski et al. | |
| 2011/0217667 A1 | 9/2011 | Groscruth | |
| 2011/0257653 A1 | 10/2011 | Hughes | |
| 2012/0065496 A1 | 3/2012 | Stratton | |
| 2012/0115107 A1 | 5/2012 | Adams | |
| 2012/0259204 A1 | 10/2012 | Carrat et al. | |
| 2012/0265051 A1 | 10/2012 | Fischer et al. | |
| 2012/0283637 A1 | 11/2012 | Cohen | |
| 2013/0063558 A1 | 3/2013 | Phipps | |
| 2013/0258353 A1 | 10/2013 | Kosmecki et al. | |
| 2014/0030669 A1 | 1/2014 | Hey et al. | |

FOREIGN PATENT DOCUMENTS

| | | |
|---|---|---|
| DE | 102009009158 | 9/2010 |
| DE | 2010042540 | 4/2012 |
| DE | 10 2011 012 460.8 | 8/2012 |
| EP | 1527417 | 9/2011 |
| FR | 2 929 794 | 10/2009 |
| GB | 2 416 949 | 2/2006 |
| JP | 2000046546 | 2/2000 |
| JP | 2007253748 | 10/2007 |
| JP | 2009172411 | 5/2009 |
| WO | 1999/27839 | 6/1999 |
| WO | 2002/076302 | 10/2002 |
| WO | 2008/009136 | 1/2008 |
| WO | 2010/086374 | 5/2010 |
| WO | 2011113441 | 9/2011 |
| WO | 2013144939 | 4/2012 |
| WO | 2012068679 | 5/2012 |
| WO | 2012095642 | 7/2012 |
| WO | 2012/149548 | 11/2012 |
| WO | 2012149548 | 11/2012 |
| WO | 2013096766 | 6/2013 |
| WO | 2011/109041 | 10/2013 |
| WO | 2011109041 | 10/2013 |
| WO | 2013144208 | 10/2013 |

OTHER PUBLICATIONS

European Patent Office, International Written Opinion, dated Sep. 3, 2013 (PCT/IL2013/000032).
European Patent Office, International Search Report, dated Sep. 16, 2013 (PCT/EP2013/056525).
European Patent Office, International Search Report, dated Sep. 17, 2013 (PCT/IL2013/000031).
Applicant's Attorney, Prosecution of U.S. Appl. No. 13/571,284, from First Office Action dated Aug. 15, 2013 to Amendment with Request for Continued Examination dated Feb. 26, 2014.
European Patent Office, International Search Report, dated Mar. 4, 2013 (PCT/IL2012/000363).
European Patent Office, International Written Opinion, dated Mar. 4, 2013 (PCT/IL2012/000363).
European Patent Office, International Search Report, dated Feb. 18, 2014 (PCT/EP2013/073416).
European Patent Office, International Written Opinion, dated Feb. 18, 2014 (PCT/EP2013/073416).

(56) References Cited

OTHER PUBLICATIONS

European Patent Office, International Search Report, International Application No. PCT/EP2013/073401, Navigate Surgical Technologies, Inc., dated Mar. 19, 2014.
European Patent Office, Written Opinion of the International Searching Authority, International Application No. PCT/EP2013/073401, Navigate Surgical Technologies, Inc., dated Mar. 19, 2014.
European Patent Office, Written Opinion of the International Searching Authority, International Application No. PCT/IL2015/050400, Navigate Surgical Technologies, Inc., dated Jul. 16, 2015.
European Patent Office, International Search Report, International Application No. PCT/IL2015/050400, Navigate Surgical Technologies, Inc., dated Jul. 16, 2015.
USPTO, Non-Final Office Action for U.S. Appl. No. 13/744,967, dated Jun. 30, 2015.
USPTO, Non-Final Office Action for U.S. Appl. No. 13/745,249, dated Jun. 30, 2015.
USPTO, Final Office Action for U.S. Appl. No. 13/745,763, dated Jul. 8, 2015.
Arizona Center for Laser Dentistry, Root Canals at the Arizona Center for Laser Dentistry, Captured via web.archive.org on Dec. 19, 2010, retrieved Jun. 2, 2015.
USPTO, Non-Final Office Action for U.S. Appl. No. 13/822,358, dated Feb. 13, 2015.
USPTO, Response to Non-Final Office Action for U.S. Appl. No. 13/745,763, dated Mar. 25, 2015.
Japanese Patent Office (JPO) Notice of Preliminary Rejection,Japan Patent Application No. 2014-537811, Based upon PCT/IL2012/000363, dated Jan. 25, 2016, which claims priority to U.S. Appl. No. 13/571,284, now U.S. Pat. No. 8,938,282.
Japanese Patent Office (JPO) Notice of Preliminary Rejection,Japanese Patent Application No. 2015-541159, Based upon PCT/EP2013/0073401, dated Mar. 1, 2016, which claims priority to U.S. Appl. No. 14/562,691, now U.S. Pat. No. 8,908,918.
European Patent Office, International Written Opinion, dated Sep. 29, 2014 (PCT/IB2014/060403).
European Patent Office, International Written Opinion, dated Oct. 17, 2014 (PCT/EP2014/067280).
European Patent Office, International Search Report, dated Jul. 17, 2014 (PCT/EP2014/058406).
European Patent Office, International Written Opinion, dated Aug. 18, 2014 (PCT/EP2014/058406).
European Patent Office, International Written Opinion, dated Jul. 30, 2014 (PCT/EP2014/057656).
European Patent Office, International Written Opinion, dated Jul. 30, 2014 (PCT/EP2014/060018).
International Search Report and Written Opinion for PCT/EP2014/067279, dated Nov. 10, 2014.
International Search Report and Written Opinion for PCT/EP2014/067280, dated Oct. 27, 2014.
Office Action in related U.S. Appl. No. 13/735,487 dated Nov. 14, 2014.
Office Action in related U.S. Appl. No. 13/745,763 dated Dec. 29, 2014.

* cited by examiner

METHOD FOR DETERMINING THE LOCATION AND ORIENTATION OF A FIDUCIAL REFERENCE

CROSS-REFERENCE TO RELATED APPLICATIONS

The present application claims priority under 35 U.S.C. § 120 of U.S. patent application Ser. No. 14/226,708, filed Mar. 26, 2014, U.S. patent application Ser. No. 14/562,691, filed May 12, 2014, which is a continuation-in-part of International Patent Application Serial Number PCT/EP2013/073401, filed on Nov. 8, 2013, which is a continuation-in-part of U.S. patent application Ser. No. 13/713,165, filed Dec. 13, 2012, and under 35 U.S.C. § 119 of U.S. Provisional Patent Application Ser. No. 61/724,024, filed Nov. 8, 2012, 61/803,040, filed Mar. 18, 2013, and 61/865,508, filed Aug. 13, 2013, the disclosures of which are incorporated by reference herein.

BACKGROUND OF THE INVENTION

Field of the Invention

The invention relates to location monitoring hardware and software systems. More specifically, the invention relates to determining the location and orientation of fiducial references during medical procedures.

Description of the Related Art

Visual and other sensory systems for observing and monitoring surgical procedures are known in the art. With such observation and monitoring systems, computer aided surgeries are now possible, and in fact are being routinely performed. In such procedures, the computer software interacts with both clinical images of the patient and observed surgical images from the current surgical procedure to provide guidance to the physician in conducting the surgery. For example, in one known system a carrier assembly bears at least one fiducial marker onto an attachment element in a precisely repeatable position with respect to a patient's jaw bone, employing the carrier assembly for providing registration between the fiducial marker and the patient's jaw bone and implanting the tooth implant by employing a tracking system which uses the registration to guide a drilling assembly. With this relatively new computer implemented technology, further improvements may further advance the effectiveness of surgical procedures.

SUMMARY OF THE INVENTION

A method for determining the location and orientation in three dimensions of a fiducial reference comprises disposing the fiducial reference to render a part of the fiducial reference observable by a tracker; obtaining from the tracker scan data of the part of the fiducial reference that is observable by the tracker; obtaining from a database predetermined geometric information about location points on the fiducial reference, the geometric information comprising three-dimensional coordinates of the location points relative to the structure of the fiducial reference; identifying within the scan data at least three location points having coordinates arranged along at least two non-parallel lines in the predetermined geometric information; and determining the three-dimensional location and orientation of the fiducial reference from the scan data and from the coordinates of the at least three identified location points in the predetermined geometric information. The at least three location points may comprise a plurality of location points and the plurality of points may be distributed in three dimensions. The at least three location points may be four location points having coordinates arranged along two non-parallel lines. The method may further comprise storing the predetermined geometric information in the database.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
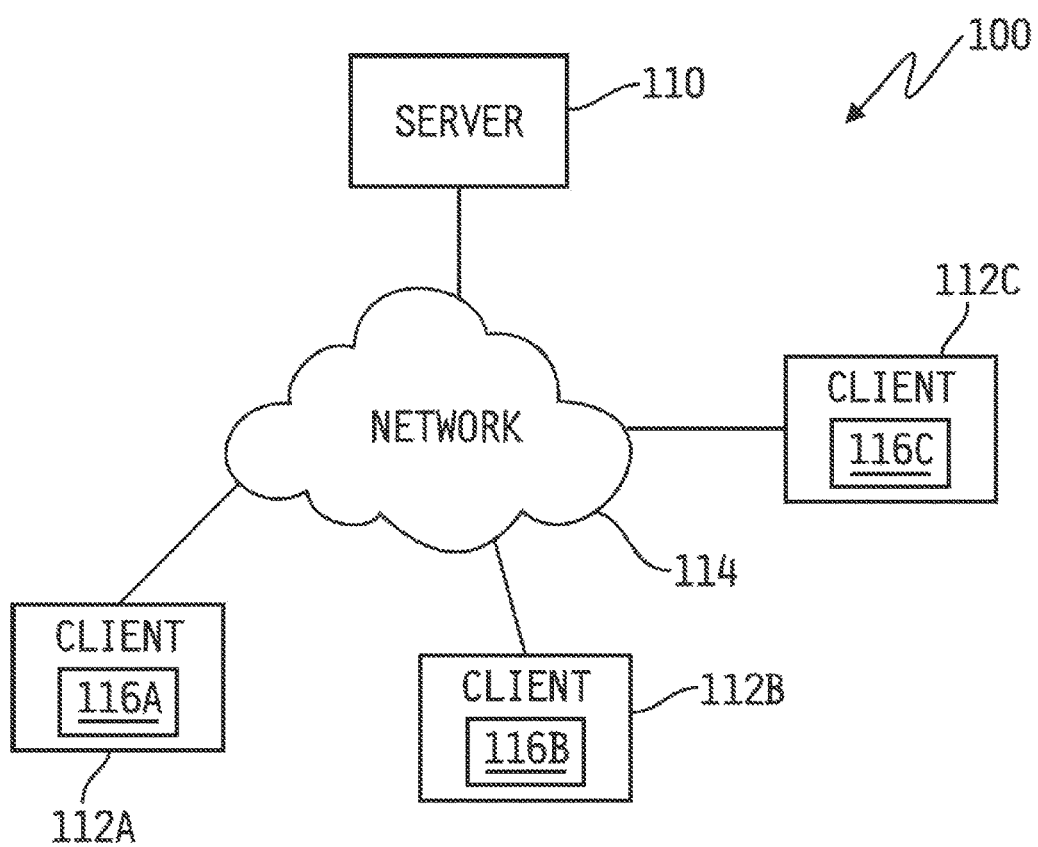
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The detailed descriptions that follow are presented in part in terms of algorithms and symbolic representations of operations on data bits within a computer memory representing alphanumeric characters or other information. The hardware components are shown with particular shapes and relative orientations and sizes using particular scanning techniques, although in the general case one of ordinary skill recognizes that a variety of particular shapes and orientations and scanning methodologies may be used within the teaching of the present invention. A computer generally includes a processor for executing instructions and memory for storing instructions and data, including interfaces to obtain and process imaging data. When a general-purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements that impart or manifest a physical organization on the information stored in memory. More than mere abstraction, the data structures are specific electrical or magnetic structural elements in memory, which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein that form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipment through signals configured to particular protocols, which may or may not require specific hardware or programming to interact. In particular, various general-purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object that may collect and transmit observed data from the physical device to the software system. Such observed data may be accessed from the physical object and/or the software object merely as an item of convenience; therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of a system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions, which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data, which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information, which is formatted in a Standard Generalized Markup Language ("SGML") or a HyperText Markup Language ("HTML"), both being scripting languages, which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data (CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system, which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

The terms "scan," "fiducial reference", "fiducial location", "marker," "tracker" and "image information" have particular meanings in the present disclosure. For purposes of the present disclosure, "scan" or derivatives thereof refer to x-ray, magnetic resonance imaging (MRI), computerized tomography (CT), sonography, cone beam computerized tomography (CBCT), or any system that produces a quantitative spatial representation of a patient. The term "fiducial reference" or simply "fiducial" refers to an object or reference on the image of a scan that is uniquely identifiable as a fixed recognizable point. In the present specification the term "fiducial location" refers to a useful location to which a fiducial reference is attached. A "fiducial location" will typically be proximate a surgical site. The term "marker" or "tracking marker" refers to an object or reference that may be perceived by a sensor proximate to the location of the surgical or dental procedure, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. The term "image information" is used in the present specification to describe information obtained by the tracker, whether optical or otherwise, and usable for determining the location of the markers and their orientation and movement continually in 'real time' during a procedure.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
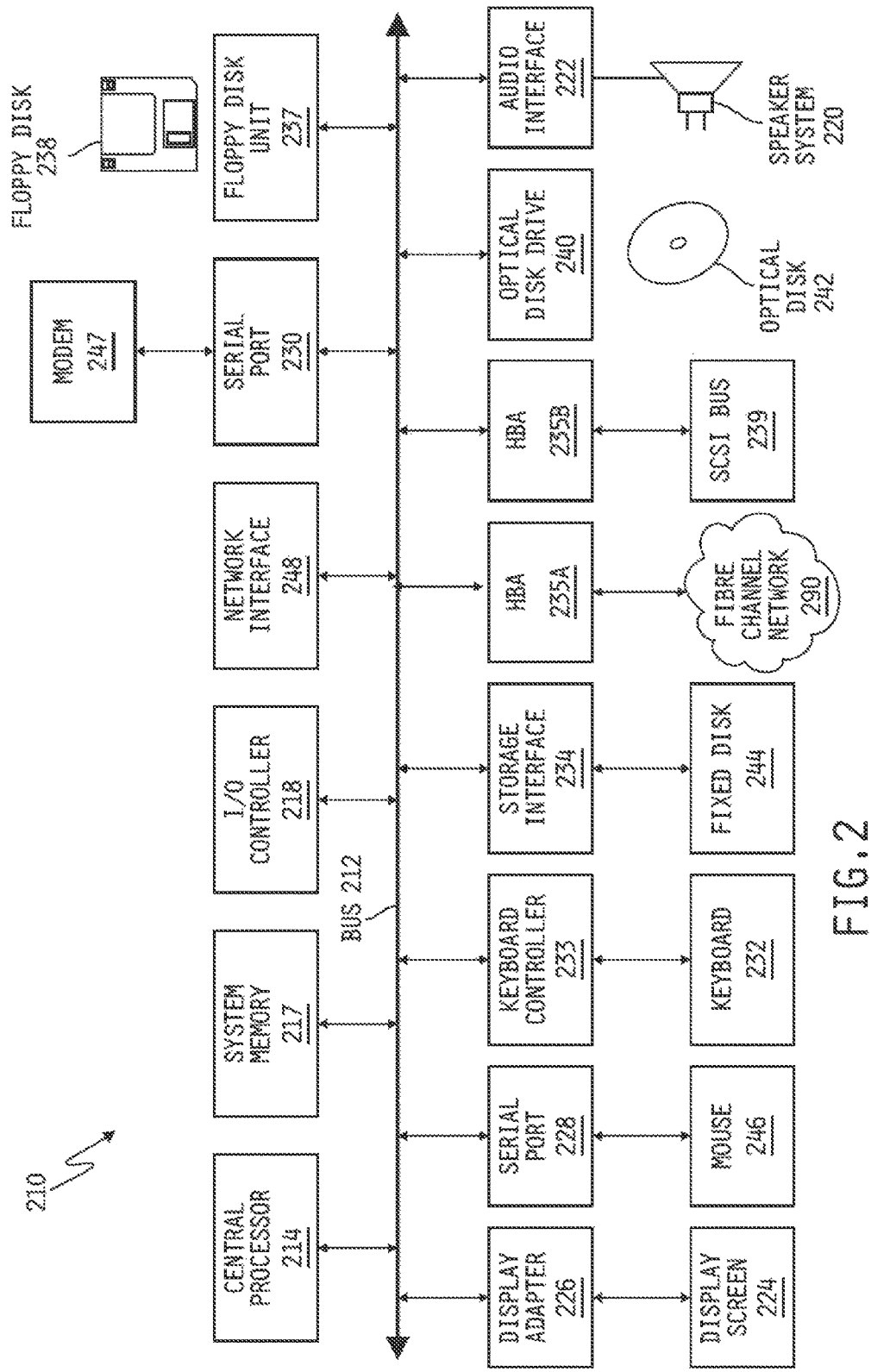
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized as controller and display in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS), which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an Internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on), including the hardware components of FIGS. 3A-I, which alternatively may be in communication with associated computational resources through local, wide-area, or wireless networks or communications systems. Thus, while the disclosure may generally discuss an embodiment where the hardware components are directly connected to computing resources, one of ordinary skill in this area recognizes that such hardware may be remotely connected with computing resources. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above-described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

The present invention relates to a surgical hardware and software monitoring system and method which allows for surgical planning while the patient is available for surgery, for example while the patient is being prepared for surgery so that the system may model the surgical site. The system uses a particularly configured piece of hardware, represented as fiducial key 10 in FIG. 3A, to orient tracking marker 12 of the monitoring system with regard to the critical area of the surgery. Fiducial key 10 is attached to a location near the intended surgical area, in the exemplary embodiment of the dental surgical area of FIG. 3A, fiducial key 10 is attached to a dental splint 14. Tracking marker 12 may be connected to fiducial key 10 by tracking pole 11. In embodiments in which the fiducial reference is directly visible to a suitable tracker (see for example FIG. 5 and FIG. 6) that acquires image information about the surgical site, a tracking marker may be attached directly to the fiducial reference. For example a dental surgery, the dental tracking marker 12 may be used to securely locate the fiducial 10 near the surgical area. The fiducial key 10 may be used as a point of reference, or a fiducial, for the further image processing of data acquired from tracking marker 12 by the tracker.

In other embodiments additional tracking markers 12 may be attached to items independent of the fiducial key 10 and any of its associated tracking poles 11 or tracking markers 12. This allows the independent items to be tracked by the tracker. Further embodiments of such additional tracking markers are discussed in detail below at the hand of FIGS. 6 and 7.

In a further embodiment at least one of the items or instruments near the surgical site may optionally have a tracker attached to function as tracker for the monitoring system of the invention and to thereby sense the orientation and the position of the tracking marker 12 and of any other additional tracking markers relative to the scan data of the surgical area. By way of example, the tracker attached to an instrument may be a miniature digital camera and it may be attached, for example, to a dentist's drill. Any other markers to be tracked by the tracker attached to the item or instrument must be within the field of view of the tracker.

Using the dental surgery example, the patient is scanned to obtain an initial scan of the surgical site. The particular configuration of fiducial key 10 allows computer software stored in memory and executed in a suitable controller, for example processor 214 and memory 217 of computer 210 of FIG. 2, to recognize its relative position within the surgical site from the scan data, so that further observations may be made with reference to both the location and orientation of fiducial key 10. In some embodiments, the fiducial reference includes a marking that is apparent as a recognizable identifying symbol when scanned. In other embodiments, the fiducial reference includes a shape that is distinct in the sense that the body apparent on the scan has an asymmetrical form allowing the front, rear, upper, and lower, and left/right defined surfaces that may be unambiguously determined from the analysis of the scan, thereby to allow the determination not only of the location of the fiducial reference, but also of its orientation.

In addition, the computer software may create a coordinate system for organizing objects in the scan, such as teeth, jaw bone, skin and gum tissue, other surgical instruments, etc. The coordinate system relates the images on the scan to the space around the fiducial and locates the instruments bearing markers both by orientation and position. The model generated by the monitoring system may then be used to check boundary conditions, and in conjunction with the tracker display the arrangement in real time on a suitable display, for example display 224 of FIG. 2.

In one embodiment, the computer system has a predetermined knowledge of the physical configuration of fiducial key 10 and examines slices/sections of the scan to locate fiducial key 10. Locating of fiducial key 10 may be on the basis of its distinct shape, or on the basis of distinctive identifying and orienting markings upon the fiducial key or on attachments to the fiducial key 10 as tracking marker 12. Fiducial key 10 may be rendered distinctly visible in the scans through higher imaging contrast by the employ of radio-opaque materials or high-density materials in the construction of the fiducial key 10. In other embodiments the material of the distinctive identifying and orienting markings may be created using suitable high density or radio-opaque inks or materials.

Once fiducial key 10 is identified, the location and orientation of the fiducial key 10 is determined from the scan segments, and a point within fiducial key 10 is assigned as the center of the coordinate system. The point so chosen may be chosen arbitrarily, or the choice may be based on some useful criterion. A model is then derived in the form of a transformation matrix to relate the fiducial system, being fiducial key 10 in one particular embodiment, to the coordinate system of the surgical site. The resulting virtual construct may be used by surgical procedure planning software for virtual modeling of the contemplated procedure, and may alternatively be used by instrumentation software for the configuration of the instrument, for providing imaging assistance for surgical software, and/or for plotting trajectories for the conduct of the surgical procedure.

In some embodiments, the monitoring hardware includes a tracking attachment to the fiducial reference. In the embodiment pertaining to dental surgery the tracking attachment to fiducial key 10 is tracking marker 12, which is attached to fiducial key 10 via tracking pole 11. Tracking marker 12 may have a particular identifying pattern. The trackable attachment, for example tracking marker 12, and even associated tracking pole 11 may have known configurations so that observational data from tracking pole 11 and/or tracking marker 12 may be precisely mapped to the coordinate system, and thus progress of the surgical procedure may be monitored and recorded. For example, as particularly shown in FIG. 3J, fiducial key 10 may have hole 15 in a predetermined location specially adapted for engagement with insert 17 of tracking pole 11. In such an arrangement, for example, tracking poles 11 may be attached with a low force push into hole 15 of fiducial key 10, and an audible haptic notification may thus be given upon successful completion of the attachment.

It is further possible to reorient the tracking pole during a surgical procedure. Such reorientation may be in order to change the location of the procedure, for example where a dental surgery deals with teeth on the opposite side of the mouth, where a surgeon switches hands, and/or where a second surgeon performs a portion of the procedure. For example, the movement of the tracking pole may trigger a re-registration of the tracking pole with relation to the coordinate system, so that the locations may be accordingly adjusted. Such a re-registration may be automatically initiated when, for example in the case of the dental surgery embodiment, tracking pole 11 with its attached tracking marker 12 are removed from hole 15 of fiducial key 10 and another tracking marker with its associated tracking pole is connected to an alternative hole on fiducial key 10. Additionally, boundary conditions may be implemented in the software so that the user is notified when observational data approaches and/or enters the boundary areas.

In a further embodiment of the system utilizing the invention, a surgical instrument or implement, herein termed a "hand piece" (see FIGS. 5, 6 and 7), may also have a particular configuration that may be located and tracked in the coordinate system and may have suitable tracking markers as described herein. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path.

Figure 3A:
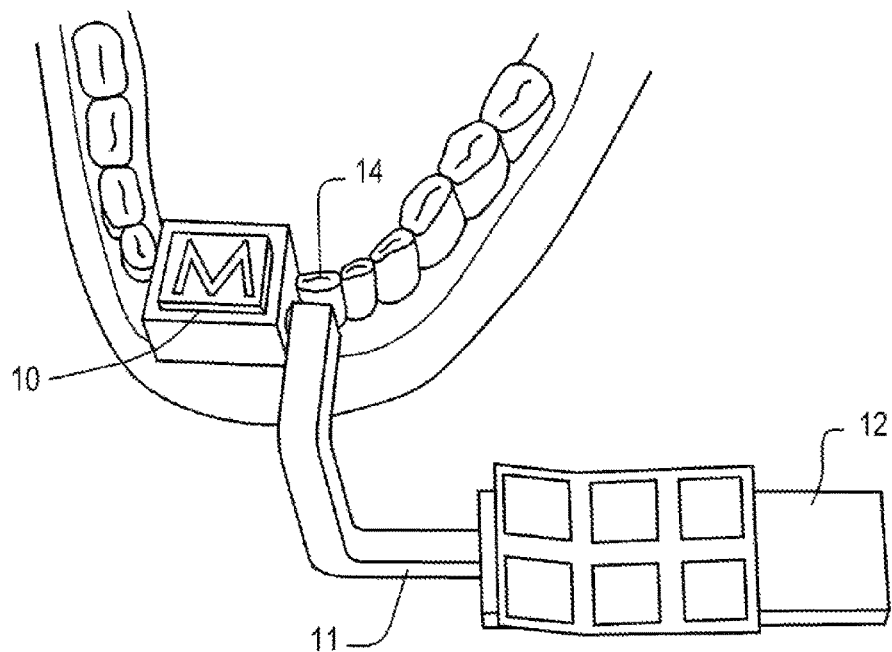
FIGS. 3A-J are drawings of hardware components of the surgical monitoring system according to embodiments of the invention.
Figure 3B:
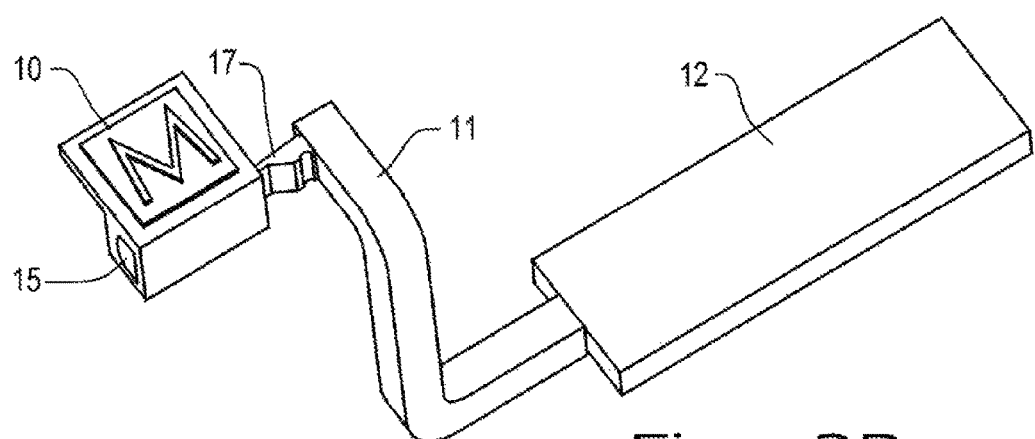
Figure 3C:
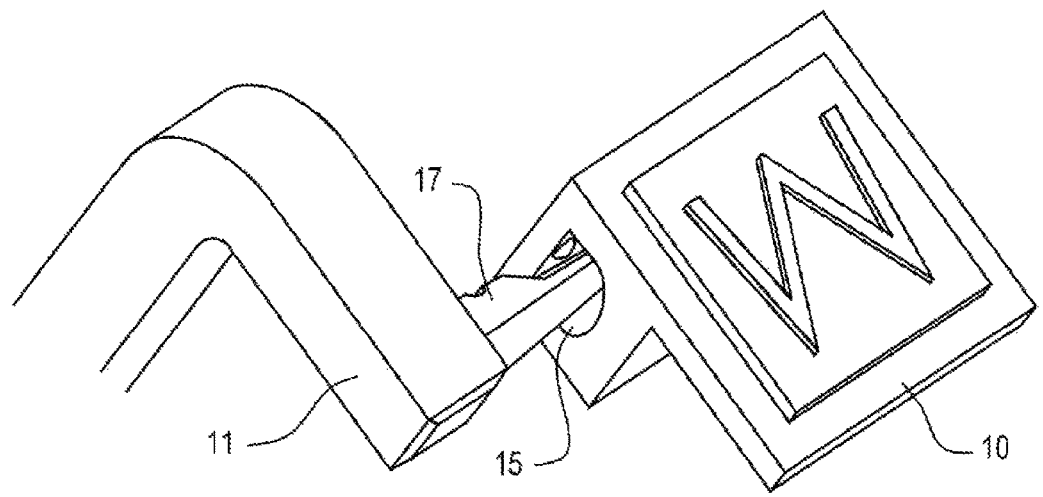
Figure 3D:
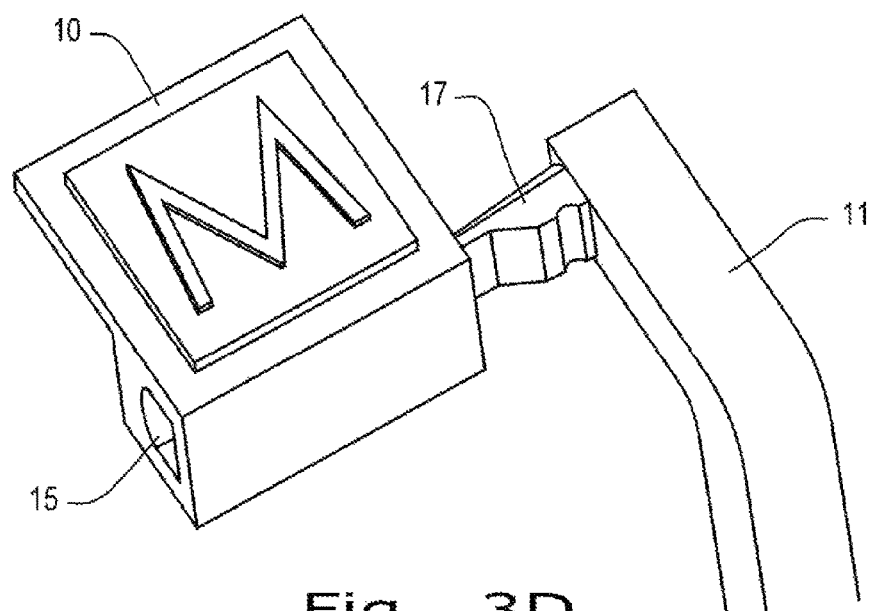
Figure 3E:
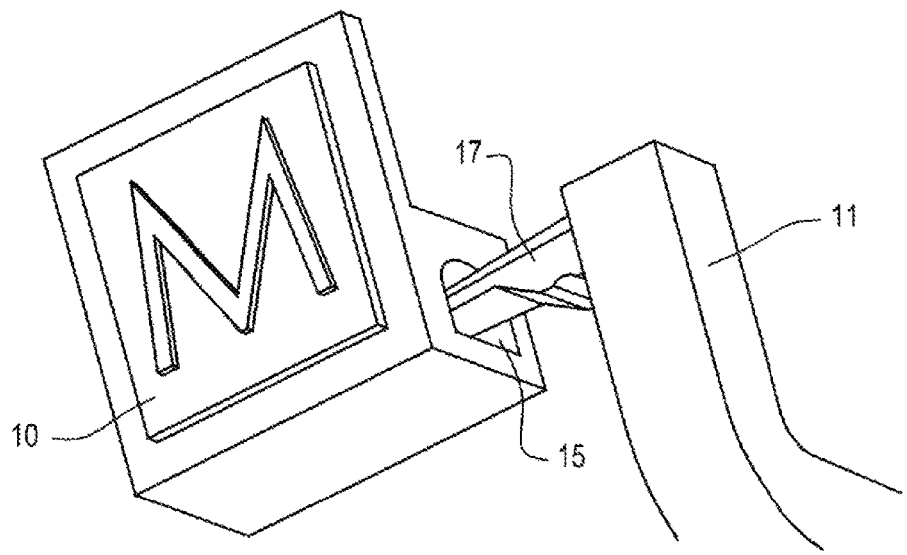
Figure 3F:
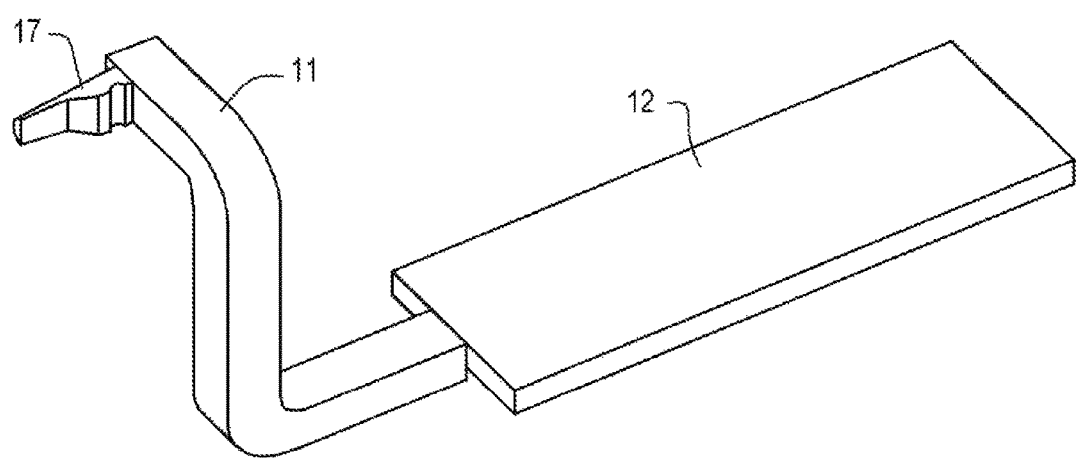
Figure 3G:
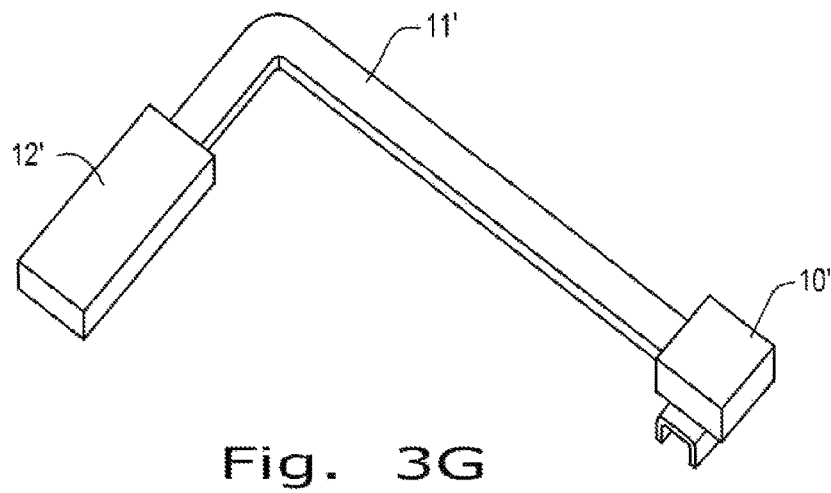
Figure 3H:
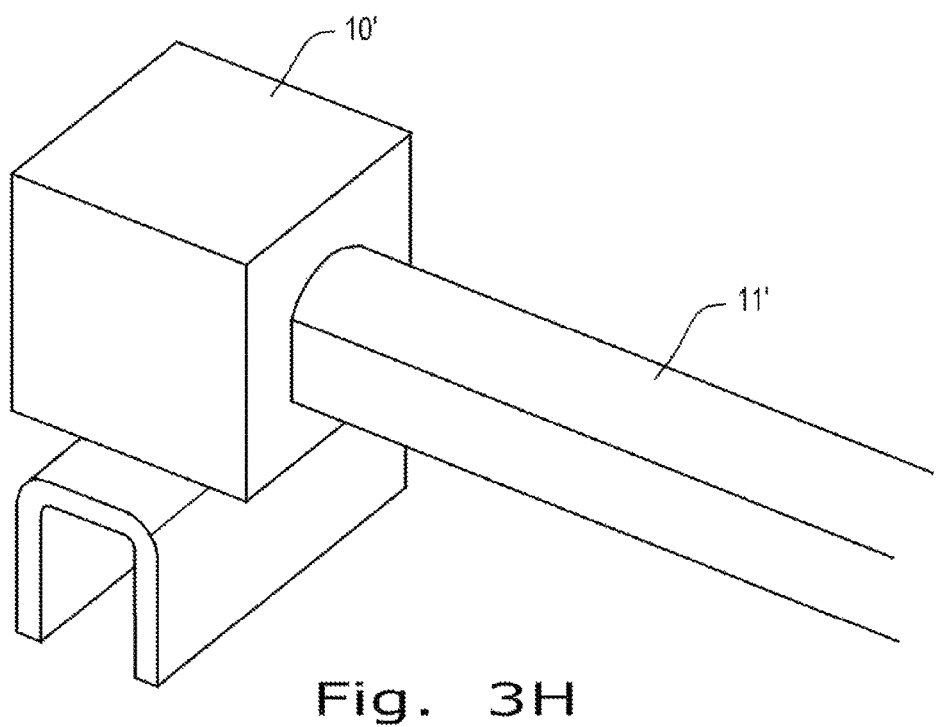
Figure 3I:
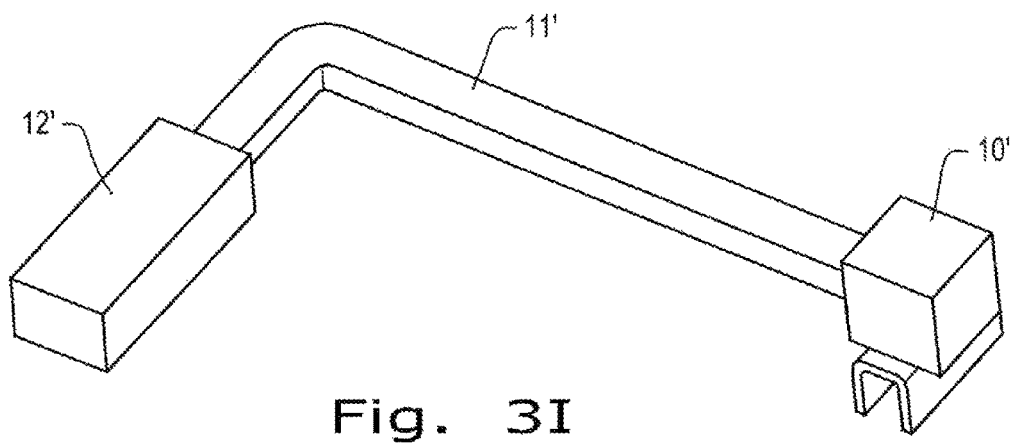
Figure 3J:
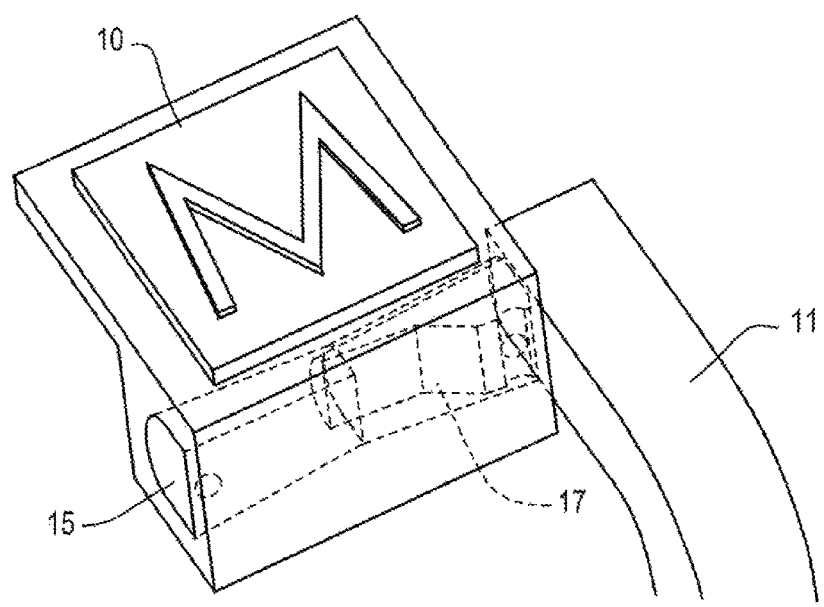

An alternative embodiment of some hardware components are shown in FIGS. 3G-I. Fiducial key 10' has connection elements with suitable connecting portions to allow a tracking pole 11' to position a tracking marker 12' relative to the surgical site. Conceptually, fiducial key 10' serves as an anchor for pole 11' and tracking marker 12' in much the same way as the earlier embodiment, although it has a distinct shape. The software of the monitoring system is pre-programmed with the configuration of each particularly identified fiducial key, tracking pole, and tracking marker, so that the location calculations are only changed according to the changed configuration parameters.

The materials of the hardware components may vary according to regulatory requirements and practical considerations. Generally, the key or fiducial component is made of generally radio opaque material such that it does not produce noise for the scan, yet creates recognizable contrast on the scanned image so that any identifying pattern associated with it may be recognized. In addition, because it is generally located on the patient, the material should be lightweight and suitable for connection to an apparatus on the patient. For example, in the dental surgery example, the materials of the fiducial key must be suitable for connection to a plastic splint and suitable for connection to a tracking pole. In the surgical example the materials of the fiducial key may be suitable for attachment to the skin or other particular tissue of a patient.

The tracking markers are clearly identified by employing, for example without limitation, high contrast pattern engraving. The materials of the tracking markers are chosen to be capable of resisting damage in autoclave processes and are compatible with rigid, repeatable, and quick connection to a connector structure. The tracking markers and associated tracking poles have the ability to be accommodated at different locations for different surgery locations, and, like the fiducial keys, they should also be relatively lightweight as they will often be resting on or against the patient. The tracking poles must similarly be compatible with autoclave processes and have connectors of a form shared among tracking poles.

The tracker employed in tracking the fiducial keys, tracking poles and tracking markers should be capable of tracking with suitable accuracy objects of a size of the order of 1.5 square centimeters. The tracker may be, by way of example without limitation, a stereo camera or stereo camera pair. While the tracker is generally connected by wire to a computing device to read the sensory input, it may optionally have wireless connectivity to transmit the sensory data to a computing device.

In embodiments that additionally employ a trackable piece of instrumentation, such as a hand piece, tracking markers attached to such a trackable piece of instrumentation may also be light-weight; capable of operating in a 3 object array with 90 degrees relationship; optionally having a high contrast pattern engraving and a rigid, quick mounting mechanism to a standard hand piece. In other embodiments the tracking markers are monolithically integrated with a rigid positioning and orienting portion of the hand piece, as described in more detail at the hand of FIGS. 6 and 7.

Figure 4A:
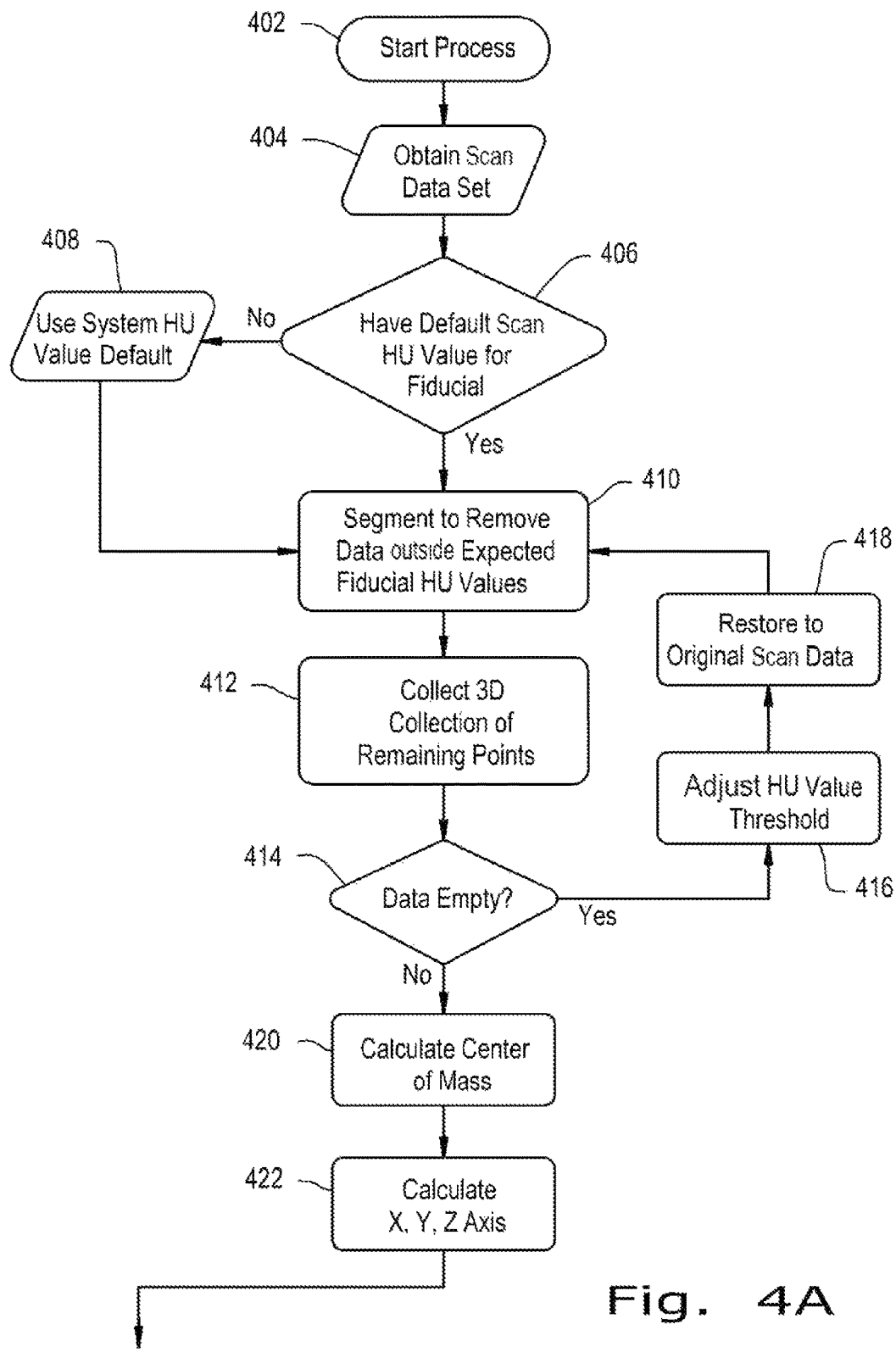
FIGS. 4A-C is a flow chart diagram illustrating one embodiment of the registering method of the present invention.
Figure 4B:
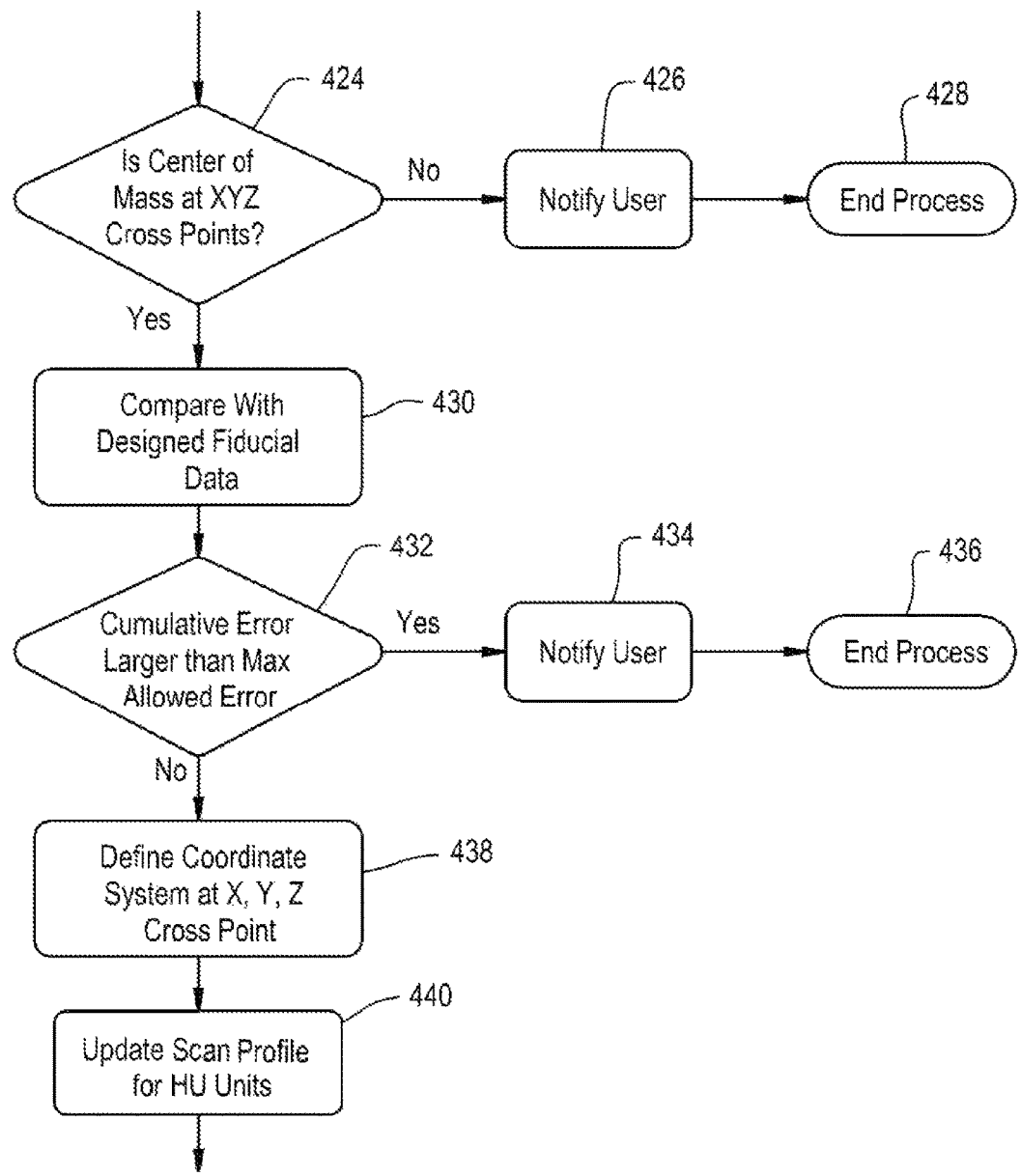
Figure 4C:
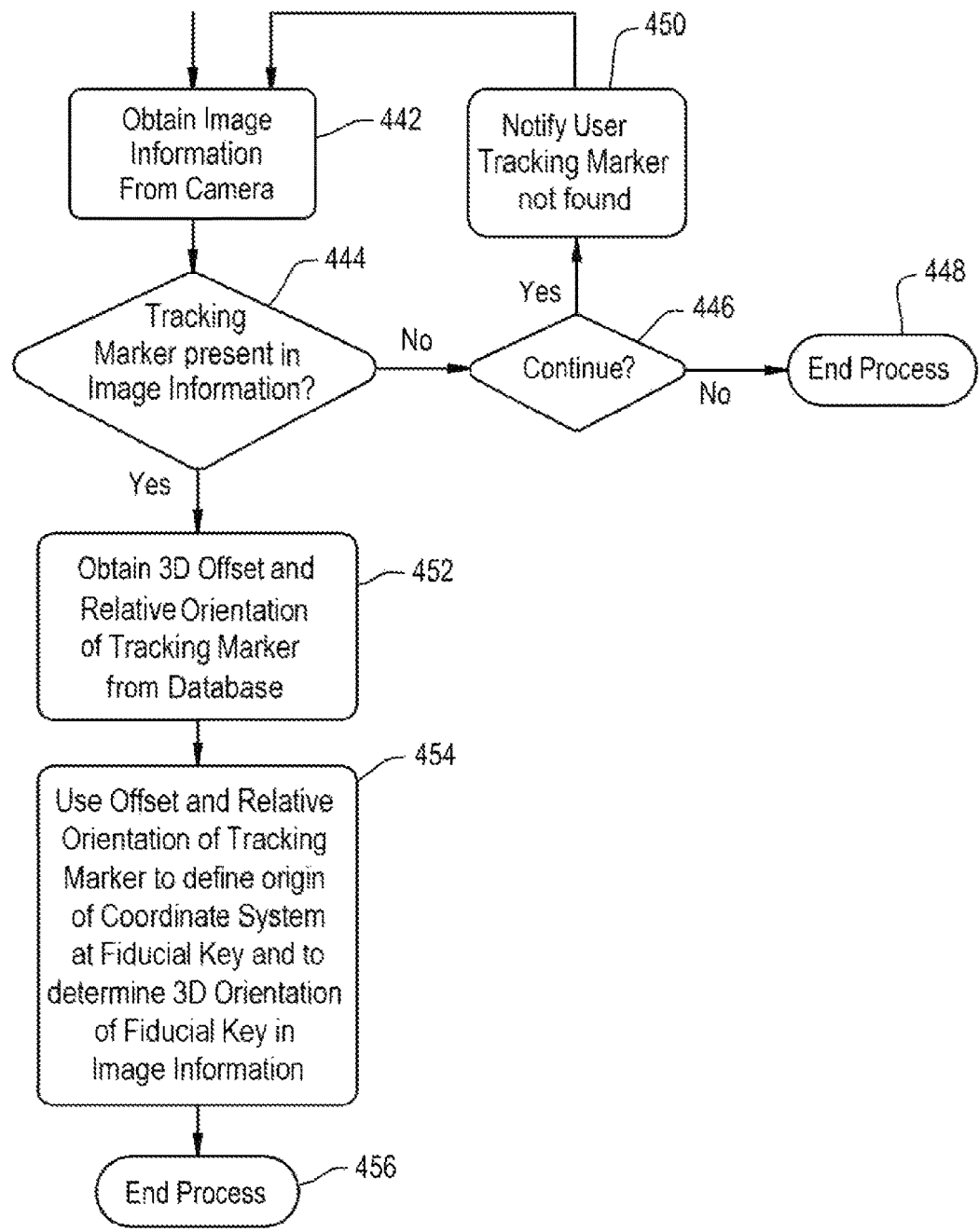

In another aspect of the invention there is presented an automatic registration method for tracking surgical activity, as illustrated in FIGS. 4A-C. FIG. 4A and FIG. 4B together present, without limitation, a flowchart of one method for determining the three-dimensional location and orientation of the fiducial reference from scan data. FIG. 4C presents a flow chart of a method for confirming the presence of a suitable tracking marker in image information obtained by the tracker and determining the three-dimensional location and orientation of the fiducial reference based on the image information.

Once the process starts [402], as described in FIGS. 4A and 4B, the system obtains a scan data set [404] from, for example, a CT scanner and checks for a default CT scan Hounsfield unit (HU) value [at 406] for the fiducial which may or may not have been provided with the scan based on a knowledge of the fiducial and the particular scanner model, and if such a threshold value is not present, then a generalized predetermined default value is employed [408]. Next the data is processed by removing scan segments with Hounsfield data values outside expected values associated with the fiducial key values [at 410], following the collection of the remaining points [at 412]. If the data is empty [at 414], the CT value threshold is adjusted [at 416], the original value restored [at 418], and the segmenting processing scan segments continues [at 410]. Otherwise, with the existing data a center of mass is calculated [at 420], along with calculating the X, Y, and Z axes [at 422]. If the center of mass is not at the cross point of the XYZ axes [at 424], then the user is notified [at 426] and the process stopped [at 428]. If the center of mass is at the XYZ cross point then the data points are compared with designed fiducial data [430]. If the cumulative error is larger than the maximum allowed error [432] then the user is notified [at 434] and the process ends [at 436]. If not, then the coordinate system is defined at the XYZ cross point [at 438], and the scan profile is updated for the HU units [at 440].

Turning now to FIG. 4C, an image is obtained from the tracker, being a suitable camera or other sensor [442]. The image information is analyzed to determine whether a tracking marker is present in the image information [444]. If not, then the user is queried [446] as to whether the process should continue or not. If not, then the process is ended [448]. If the process is to continue, then the user can be notified that no tracking marker has been found in the image information [450], and the process returns to obtaining image information [442]. If a tracking marker has been found based on the image information, or one has been attached by the user upon the above notification [450], the offset and relative orientation of the tracking marker to the fiducial reference is obtained from a suitable database [452]. The term "database" is used in this specification to describe any source, amount or arrangement of such information, whether organized into a formal multi-element or multi-dimensional database or not. A single data set comprising offset value and relative orientation may suffice in a simple implementation of this embodiment of the invention and may be provided, for example, by the user or may be within a memory unit of the controller or in a separate database or memory.

The offset and relative orientation of the tracking marker is used to define the origin of a coordinate system at the fiducial reference and to determine the three-dimensional orientation of the fiducial reference based on the image information [454] and the registration process ends [458]. In order to monitor the location and orientation of the fiducial reference in real time, the process may be looped back from step [454] to obtain new image information from the camera [442]. A suitable query point may be included to allow the user to terminate the process. Detailed methods for determining orientations and locations of predetermined shapes or marked tracking markers from image data are known to practitioners of the art and will not be dwelt upon here. The coordinate system so derived is then used for tracking the motion of any items bearing tracking markers in the proximity of the surgical site. Other registration systems are also contemplated, for example using current other sensory data rather than the predetermined offset, or having a fiducial with a transmission capacity.

Figure 5:
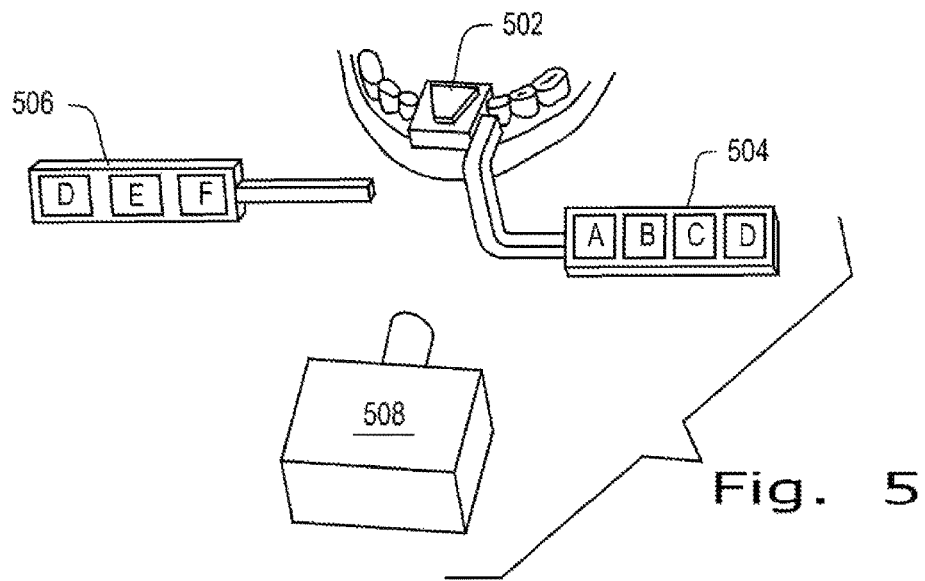
FIG. 5 is a drawing of a dental fiducial key with a tracking pole and a dental drill according to one embodiment of the present invention.

One example of an embodiment of the invention is shown in FIG. 5. In addition to fiducial key 502 mounted at a predetermined tooth and having a rigidly mounted tracking marker 504, an additional instrument or implement 506, for example a hand piece which may be a dental drill, may be observed by a camera 508 serving as tracker of the monitoring system.

Figure 6:
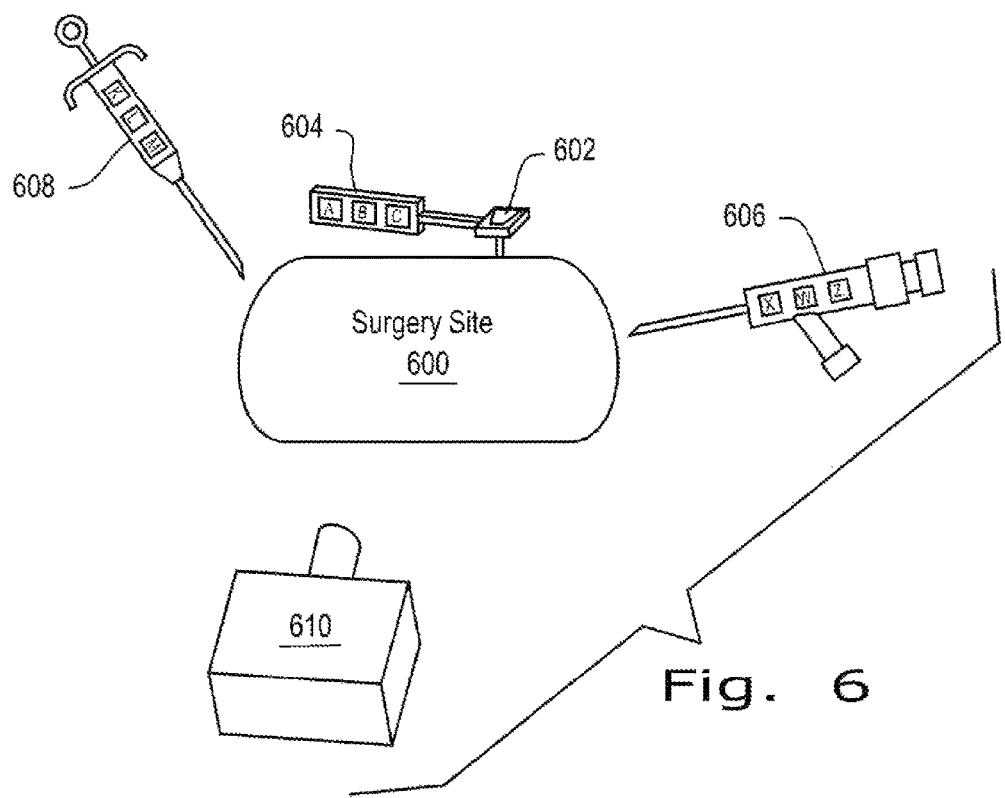
FIG. 6 is a drawing of an endoscopic surgical site showing the fiducial key, endoscope, and biopsy needle according to another embodiment of the invention.

Another example of an embodiment of the invention is shown in FIG. 6. Surgery site 600, for example a human stomach or chest, may have fiducial key 602 fixed to a predetermined position to support tracking marker 604. Other apparatus with suitable tracking markers may be in use in the process of the surgery at surgery site 600. By way of non-limiting example, endoscope 606 may have a further tracking marker, and biopsy needle 608 may also be present bearing a tracking marker at surgery site 600. Sensor 610, serving as tracker for the system, may be for example a camera, infrared sensing device, or RADAR. In particular, the tracker may be a two-dimensional imaging tracker that produces a two dimensional image of the surgery site 600 for use as image information for the purposes of embodiments of the invention, including two dimensional image information of any tracking markers in the field of view of the tracker. Surgery site 600, endoscope 606, biopsy needle 608, fiducial key 602 and tracking marker 604 may all be in the field of view of tracker 610.

Figure 7:
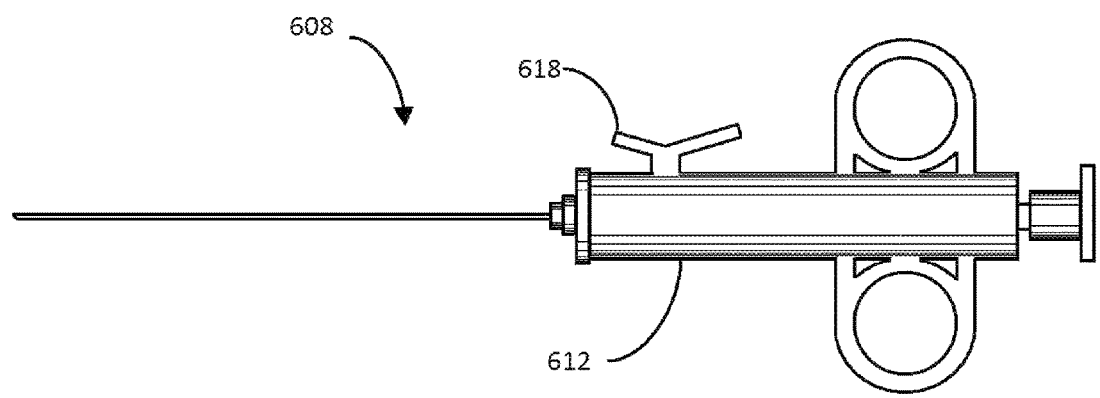
FIG. 7 is a drawing of a biopsy needle showing an embodiment of a monolithically integrated tracking marker.

FIG. 6, shows one embodiment of a tracking marker used to track biopsy needle 608. FIG. 7 shows another embodiment of a tracking marker of, for example, biopsy needle 608. In this embodiment tracking marker 618 is monolithically integrated with a rigid positioning and orienting portion of biopsy needle 608. In the present specification the phrase "monolithically integrated" is used to describe items that are fashioned together from one piece of material; this to be contrasted with a situation where the items are joined together after manufacture, either detachably or through a non-integral coupling. In this particular example a suitable rigid positioning and orienting portion of biopsy needle 608 is its handle 612. Handle 612 may, for example be molded, cast, machined or otherwise fashioned from one monolithic piece of material and tracking marker 618 is fashioned, formed or made from the same monolithic piece of material. Tracking marker 618 may be formed during the same process as that within which the rigid handle portion 612 of the biopsy needle 608 is made.

Handle 612 itself may in some embodiments comprise two or more sections, but, when assembled, the two or more sections create a rigid whole that dictates where and how the working end of the apparatus, in this case the point of biopsy needle 608, will be positioned and oriented in three dimensions relative to handle 612. To the extent that tracking marker 618 is monolithically integrated with a rigid part of the handle 612 of biopsy needle 608, and the position and orientation of monolithically integrated tracking marker 618 relative to the point of biopsy needle 608 is fixed and known, knowledge of the three-dimensional position and orientation of tracking marker 618 within the field of view of tracker 610 provides the user with the location and orientation of the point of biopsy needle 608. In such an embodiment, based on for example two halves of handle 612 of biopsy needle 608, the relavent rigid positioning and orienting portion of biopsy needle 608 is the half of handle 612 with which tracking marker 618 is monolithically integrated.

The monolithic integration of three-dimensional tracking markers with a rigid positioning and orienting portion of an instrument is not limited to surgical devices. It may be applied to any medical instrument having a suitable rigid positioning and orienting portion and, indeed, to any apparatus having a suitable rigid positioning and orienting portion.

As with tracking markers described in other embodiments, tracking marker 618 may be shaped in three dimensions so as to allow its orientation to be determined from a two-dimensional image of biopsy needle 608 within the field of view of tracker 610. In further embodiments, monolithically integrated tracking marker 618 may have a monolithically integrated marking so as to allow its orientation to be determined from a two-dimensional image of biopsy needle 608 within the field of view of tracker 610. In further embodiments tracking marker may be both shaped and marked to allow its orientation, its location, or both to be determined.

In yet further embodiments, positioning and orienting markings may be scribed, engraved, stamped, embossed or otherwise formed on tracking marker 618. Useful markings for determining the location and orientation of tracking marker 618 are described in copending U.S. patent application Ser. No. 13/713,165 titled "System and method for determining the three-dimensional location and orientation of identification markers", published as U.S. Patent Publication No. 2014/0126767 A1, which is hereby incorporated by reference in full.

The markings on tracking marker 618 as described in patent application Ser. No. 13/713,165 comprise a plurality of contrasting portions arranged in a rotationally asymmetric pattern and at least one of the contrasting portions has a perimeter that has a mathematically describable curved section. The perimeter of the contrasting portion may comprise a conic section, including for example an ellipse or a circle. The markings may be monolithically integrated with the tracking marker. In other embodiments the markings may be scribed, engraved, stamped, embossed or otherwise formed on the tracking marker 618. Geometric information about the asymmetric pattern may be stored in a database. A suitable controller, for example processor 214 and memory 217 of computer 210 of FIG. 2, may be used to compare the image information obtained from tracker 610 with the geometric information about tracking marker 618 in order to determine the three dimensional location and orientation of tracking marker 618 and its associated biopsy needle 608.

In a further aspect of the invention a method for making a three dimensionally trackable rigid positioning and orienting portion of an apparatus comprises monolithically forming a three-dimensional tracking marker integral with the rigid positioning and orienting portion of the apparatus. The method may further comprise monolithically forming positioning and orienting markings integral with the tracking marker. The method may further comprise scribing, engraving, stamping, embossing or otherwise forming positioning and orienting markings on the three-dimensional tracking marker.

Figure 8A:
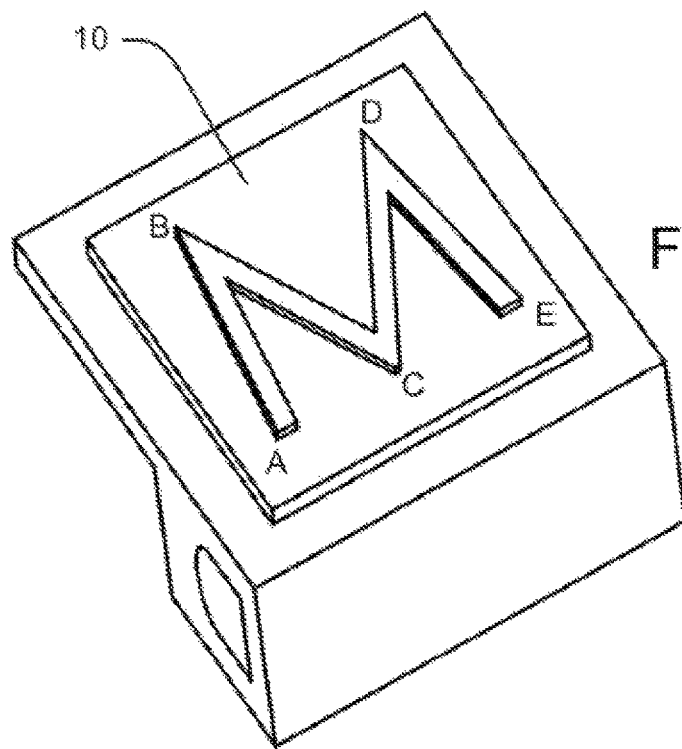
FIG. 8a is a more detailed view of the fiducial reference of FIGS. 3 A-E and FIGS. 3 G-J.

FIG. 8a shows a fiducial key 13. By way of non-limiting example, we select the fiducial key 10 already discussed with respect to FIGS. 3A-E and FIGS. 3G-J. In general, the fiducial key may be marked or shaped, or both, in order to allow its location and orientation to be determined in three dimensions. In the embodiment described herewith, fiducial key 10 is marked to allow its location and orientation to be determined in three dimensions. As shown in FIG. 8a, five identifiable location points on fiducial key 10 are shown, being marked as "A", "B", "C", "D", "E". At least five different non-parallel lines may be drawn between these highly identifiable points. At least four different distinctive triangles may be formed from lines joining the five points. It is clear that, with a minimum of three identifiable points, for example "A", "B", and "C", the position and orientation of fiducial key 10 may be determined uniquely. In the case of FIG. 8a there are several other points that may be similarly employed to form other triangles that may be used in similar fashion.

Figure 8B:
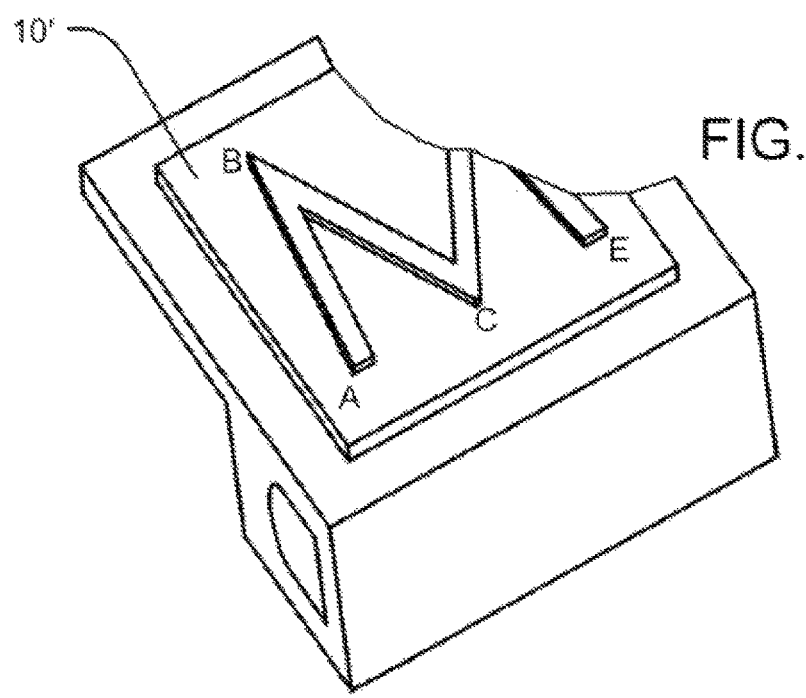
FIG. 8b shows a partial version of the fiducial reference of FIGS. 3 A-E and FIGS. 3 G-J.

We now consider FIG. 8b, which shows the same tag 10, but it is either broken or only partially observable so as to present only portion 10' for observation by a suitable tracker. The term "observable" is used here to describe the image-wise detectability of the fiducial reference by the tracker with the tracker employing whatever particular penetrating radiation it is designed to employ. Under both of these circumstances only points "A", "B", "C", and "E" are visible to a tracker (not shown in FIG. 8a). In order to fully determine the location and orientation of tag 10' in three-dimensional space, points "A" and "B", for example, together with either of points "C", or "E" suffices. The more points that are available, the more accurately the position and orientation in three dimensions may be determined.

It is clear from FIGS. 8a and 8b that the identification of two sets of points lying along two mutually non-parallel directions on fiducial reference 10, or portion 10' of fidicuial reference 10, allows the determination of the location and orientation of fiducial reference 10 in three-dimensional space.

In some embodiments, four identifiable points, distributed as two sets of two points each along two straight non-parallel lines may be employed to fully determine the three dimensional location and orientation of fiducial reference 10, or portion 10' of fiducial reference 10. Referring to FIGS. 8a and 8b, the line between points "A" and "B", on the one hand, and the line between points "C" and "E" on the other hand, may be employed in this embodiment.

The embodiment wherein three identified location points are employed is therefore merely a special a case in which two of the four points are the same point and the required two non-parallel lines share a common point.

In a more general case, the identifiable points on fiducial reference 10, or on portion 10' of fiducial reference 10, required to fully determine the location and orientation of fiducial reference 10, or portion 10' of fiducial reference 10, need not be located along two straight lines, but the three-dimensional spatial relationship between the points must be known.

The underlying requirement to fully determine the location and orientation of fiducial reference 10, or of a portion 10' of fiducial reference 10, is for there to be at least three identifiable location points, for example "A", "B", and "C", defining two non-parallel lines, observable by the tracker, and identifiable from a from a preexisting database in which their three-dimensional locations are known relative to the structure of fiducial reference 10 or 10'. In one embodiment, the specific structure of fiducial reference 10 or 10' in relation to the at least three identifiable location points is specified by the operator of the tracker, for example by data entry of the relevant parameters or by scanning fiducial reference 10 prior to its use or by scanning a replica of fiducial reference 10, so that upon recognition of at least three location points the location and orientation of fiducial reference 10 or 10' may be determined accordingly. Alternatively, the system may use information relating to the at least three identifiable location points and other image information about fiducial reference 10 or 10', for example at least a portion of an exterior edge, or specific observable shapes or markers on fiducial reference 10 or 10', may be used by image recognition software to identify a specific type or instance of a fiducial reference and match to a known image of a fiducial reference from a database of known fiducial references, wherein the database has information relating to the specific corresponding structure and relation of the at least three identifiable location points.

In general a plurality of identifiable points arranged in a general distribution on fiducial reference 10, or on a portion 10' of fiducial reference 10, may be employed, the accuracy of the method improving with the number of identifiable points employed.

In the different surgical examples described in this specification, the entire fiducial reference employed does not have to be observable to the tracker, as long as at least three pre-identified points are observable by the tracker and the three-dimensional locations of those three pre-identified points are known relative to the structure of the fiducial reference. The structure of the fiducial reference may be entered directly by the operator, or be derived from a suitable database.

More specifically, the method described above for determining the location and orientation in three dimensions of a general fiducial reference of any of the above embodiments comprises disposing the fiducial reference to render a part of the fiducial reference observable by a tracker; obtaining from the tracker scan data of the part of the fiducial reference that is observable by the tracker; obtaining predetermined geometric information about location points on the fiducial reference, the geometric information comprising three-dimensional coordinates of the location points relative to the structure of the fiducial reference; identifying within the scan data at least three location points having coordinates arranged along at least two non-parallel lines in the predetermined geometric information; and determining the three-dimensional location and orientation of the fiducial reference from the scan data and from the coordinates of the at least three identified location points in the predetermined geometric information. The at least three location points may comprise a plurality of location points and the plurality of points may be distributed in three dimensions.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for determining the location and orientation of a fiducial reference having scan data in three dimensions, the method comprising
   a. disposing the fiducial reference to render a part of the fiducial reference observable by a non-stereo tracker;
   b. obtaining from the tracker image data of the part of the fiducial reference that is observable by the tracker;
   c. obtaining predetermined geometric information about location points on the fiducial reference, the geometric information comprising three-dimensional coordinates of the location points relative to the structure of the fiducial reference;
   d. identifying within the image data at least three location points having coordinates arranged along at least two non-parallel lines in the predetermined geometric information; and
   e. determining the three-dimensional location and orientation of the fiducial reference from the scan data and from the coordinates of the at least three identified location points in the predetermined geometric information.

2. The method of claim 1, wherein the at least three location points comprise a plurality of location points.

3. The method of claim 2, wherein the plurality of points is distributed in three dimensions.

4. The method of claim 1, wherein the at least three location points are four location points having coordinates arranged along two non-parallel lines.

5. The method of claim 1, further comprising storing the predetermined geometric information in a database.

6. The method of claim 1, wherein the obtaining step includes using a database to find a match to the fiducial reference.

7. The method of claim 1, wherein the obtaining step includes scanning a replica of the fiducial reference.

8. The method of claim 1, wherein the obtaining step includes the operator entering relevant configuration parameters relating to the fiducial reference.

9. A system for determining the location and orientation of a fiducial reference in three dimensions, said system comprising:
   a computing device including a processor and associated memory; and
   a non-stereo tracker coupled to the computing device and configured to observe image data from a surgical site and send the image data from a surgical site to the computing device;
   wherein said memory stores a plurality of computing device instructions, the plurality of instructions including instructions to obtain image data from the tracker that includes at least a part of the fiducial reference that is observable by the tracker, to obtain predetermined geometric information about location points on the fiducial reference, the geometric information comprising three-dimensional coordinates of the location points relative to the structure of the fiducial reference, to identify within the image data at least three location points having coordinates arranged along at least two non-parallel lines in the predetermined geometric information, and to determine the three-dimensional location and orientation of the fiducial reference from the scan data and from the coordinates of the at least three identified location points in the predetermined geometric information.

10. A system of claim 9, wherein the at least three location points comprise a plurality of location points.

11. The system of claim 10, wherein the plurality of points is distributed in three dimensions.

12. The system of claim 9, wherein the at least three location points are four location points having coordinates arranged along two non-parallel lines.

13. The system of claim 9, further comprising storing the predetermined geometric information in a database.

14. The system of claim 9, wherein the instructions to obtain predetermined geometric information includes instructions to use a database to find a match to the fiducial reference.

15. The system of claim 9, further comprising instructions to obtain predetermined geometric information by using the tracker to obtain image data on the fiducial reference.

16. The system of claim 9, further comprising instructions to obtain predetermined geometric information by operator input of relevant configuration parameters.

* * * * *